US008426161B1

(12) United States Patent  (10) Patent No.: US 8,426,161 B1
Horton  (45) Date of Patent: *Apr. 23, 2013

(54) METHOD TO PRODUCE SUGAR WATER AND ETHANOL

(71) Applicant: Jerry W. Horton, Rush, NY (US)

(72) Inventor: Jerry W. Horton, Rush, NY (US)

(73) Assignee: Sweetwater Energy, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/646,425

(22) Filed: Oct. 5, 2012

Related U.S. Application Data

(63) Continuation of application No. 11/974,129, filed on Oct. 11, 2007, now Pat. No. 8,323,923.

(60) Provisional application No. 60/851,424, filed on Oct. 13, 2006.

(51) Int. Cl.
*C12P 1/02* (2006.01)
*C12P 7/06* (2006.01)

(52) U.S. Cl.
USPC ............................................ 435/41; 435/161

(58) Field of Classification Search .................... 435/41, 435/161
See application file for complete search history.

(56) References Cited

U.S. PATENT DOCUMENTS

| | | | |
|---|---|---|---|
| 4,048,341 A | 9/1977 | Lagerstrom et al. |
| 4,070,232 A | 1/1978 | Funk |
| 4,182,780 A | 1/1980 | Lagerstrom et al. |
| 4,201,596 A | 5/1980 | Church et al. |
| 4,350,766 A | 9/1982 | Mehlberg |
| 4,395,488 A | 7/1983 | Rowe |
| 4,414,330 A | 11/1983 | Zucker et al. |
| 4,447,534 A | 5/1984 | Moebus et al. |
| 4,478,854 A | 10/1984 | Adler-nissen et al. |
| 4,520,105 A | 5/1985 | Sinner et al. |
| 4,600,590 A | 7/1986 | Dale |
| 4,612,286 A | 9/1986 | Sherman et al. |
| 4,615,742 A | 10/1986 | Wright |
| 4,644,060 A | 2/1987 | Chou |
| 4,650,689 A | 3/1987 | Hedrick |
| 4,806,475 A | 2/1989 | Gould |
| 5,037,663 A | 8/1991 | Dale |
| 5,144,008 A | 9/1992 | Ikeda et al. |
| 5,171,592 A | 12/1992 | Holtzapple et al. |
| 5,177,008 A | 1/1993 | Kampen |
| 5,177,009 A | 1/1993 | Kampen |
| 5,473,061 A | 12/1995 | Bredereck et al. |
| 5,693,296 A | 12/1997 | Holtzapple et al. |
| 5,726,046 A | 3/1998 | Farone et al. |
| 5,846,787 A | 12/1998 | Ladisch et al. |
| 5,865,898 A | 2/1999 | Holtzapple et al. |
| 5,939,544 A | 8/1999 | Karstens et al. |
| 5,969,189 A | 10/1999 | Holtzapple et al. |
| 5,986,133 A | 11/1999 | Holtzapple et al. |
| 6,043,392 A | 3/2000 | Holtzapple et al. |
| 6,106,888 A | 8/2000 | Dale et al. |
| 6,176,176 B1 | 1/2001 | Dale et al. |
| 6,258,175 B1 | 7/2001 | Lightner |
| 6,262,313 B1 | 7/2001 | Holtzapple et al. |
| 6,365,732 B1 | 4/2002 | Van Thorre |
| 6,416,621 B1 | 7/2002 | Karstens |
| 6,478,965 B1 | 11/2002 | Holtzapple et al. |
| 6,509,180 B1 | 1/2003 | Verser et al. |
| 7,109,005 B2 | 9/2006 | Eroma et al. |
| 7,503,981 B2 | 3/2009 | Wyman et al. |
| 7,909,895 B2 | 3/2011 | Dickinson et al. |
| 7,932,063 B2 | 4/2011 | Dunson, Jr. et al. |
| 7,935,840 B2 | 5/2011 | Leveson et al. |
| 8,103,385 B2 | 1/2012 | Macharia et al. |
| 8,123,864 B2 | 2/2012 | Christensen et al. |
| 2002/0038058 A1 | 3/2002 | Holtzapple et al. |
| 2002/0164730 A1 | 11/2002 | Ballesteros Perdices et al. |
| 2002/0164731 A1 | 11/2002 | Eroma et al. |
| 2002/0192774 A1 | 12/2002 | Ahring et al. |
| 2002/0197686 A1 | 12/2002 | Lightner |
| 2003/0199049 A1 | 10/2003 | Nguyen et al. |
| 2003/0221361 A1 | 12/2003 | Russell et al. |
| 2003/0224088 A1 | 12/2003 | Burdick |
| 2004/0152881 A1 | 8/2004 | Holtzapple et al. |

(Continued)

FOREIGN PATENT DOCUMENTS

CA  1267407 B  4/1990
EP  1259466 B1  10/2008

(Continued)

OTHER PUBLICATIONS

Notice of allowance dated Oct. 15, 2012 for U.S. Appl. No. 11/974,129.

(Continued)

*Primary Examiner* — Jon P Weber
*Assistant Examiner* — Kailash C Srivastava
(74) *Attorney, Agent, or Firm* — Wilson Sonsini Goodrich & Rosati

(57) ABSTRACT

A method for producing ethanol comprising the steps of providing feedstock, processing the feedstock at a feedstock processing plant adapted to produce sugar water and wet animal feed, separating the sugar water and wet animal feed, transporting the sugar water from the feedstock processing plant to an ethanol producing plant, and producing ethanol from the sugar water. A system for producing ethanol comprising a feedstock provider adapted to provide feedstock, feedstock, a feedstock processing plant adapted to produce sugar water and wet animal feed from the feedstock, a means for transporting the sugar water, and an ethanol producing plant adapted to produce ethanol from the sugar water.

20 Claims, 2 Drawing Sheets

U.S. PATENT DOCUMENTS

| | | | |
|---|---|---|---|
| 2004/0168960 | A1 | 9/2004 | Holtzapple et al. |
| 2004/0171136 | A1 | 9/2004 | Holtzapple et al. |
| 2005/0054064 | A1 | 3/2005 | Talluri et al. |
| 2005/0244934 | A1 | 11/2005 | Foody et al. |
| 2006/0003064 | A1 | 1/2006 | James |
| 2006/0024801 | A1 | 2/2006 | Holtzapple et al. |
| 2006/0069244 | A1 | 3/2006 | Holtzapple et al. |
| 2006/0188980 | A1 | 8/2006 | Holtzapple et al. |
| 2006/0251764 | A1 | 11/2006 | Abbas et al. |
| 2007/0037259 | A1 | 2/2007 | Hennessey et al. |
| 2007/0118916 | A1 | 5/2007 | Puzio et al. |
| 2007/0148750 | A1 | 6/2007 | Hoshino et al. |
| 2007/0275447 | A1 | 11/2007 | Lewis et al. |
| 2008/0121359 | A1 | 5/2008 | Holtzapple et al. |
| 2009/0064566 | A1 | 3/2009 | Brummerstedt Iversen et al. |
| 2010/0144001 | A1 | 6/2010 | Horton |
| 2011/0258911 | A1 | 10/2011 | Hanson et al. |

FOREIGN PATENT DOCUMENTS

| | | | |
|---|---|---|---|
| EP | 1307735 | B1 | 11/2008 |
| EP | 1299170 | B1 | 8/2010 |
| WO | WO 01/60752 | A1 | 8/2001 |
| WO | WO 02/00324 | A1 | 1/2002 |
| WO | WO 02/01220 | A2 | 1/2002 |
| WO | WO 02/01220 | A3 | 9/2002 |
| WO | WO 2005/118828 | A1 | 12/2005 |

OTHER PUBLICATIONS

Office action dated May 24, 2010 for U.S. Appl. No. 11/974,129.

Office action dated Jul. 6, 2012 for U.S. Appl. No. 11/974,129.

Office action dated Oct. 3, 2012 for U.S. Appl. No. 12/633,555.

Office action dated Nov. 8, 2010 for U.S. Appl. No. 11/974,129.

Sluiter, et al. Determination of structural carbohydrates and lignin in biomass. National Renewable Energy Laboratory. Technical report NREL/TP-510-42618. Revised Jun. 2010.

Alcohol and Tobacco Tax and Trade Bureau, treasury. 27 C.F.R. § 19.134 Bonded warehouse not on premises qualified for production of spirits, p. 381, Apr. 1, 1997 revision.

Boggan. 2003. Alcohol, Chemistry and You Sources and Uses of Ethyl Alcohol. Kennesaw State University, pp. 1-5, Printed May 17, 2010. http://www.chemcases.com/alcohol/alc-03.htm/.

Dowe et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages).

Gum,et al. Structural characterization of a glycoprotein cellulase, 1,4-beta-D-glucan cellubiohydrolase C from trichodermaviride. Biochem. Biophys. Acta. 1976; 446:370-86.

International search report and written opinion dated Jan. 26, 2009 for PCT/US2009/67221.

Jones et al., (1994, Ethanolic Fermentation of Blackstrap Molasses and Sugarcane Juice Using Very High Gravity Technology. J. Agric. Food Chem, vol. 42, pp. 1242-1246).

Kim, et al. Lime pretreatment and enzymatic hydrolysis of corn stover. Bioresour Technol. Dec. 2005;96(18):1994-2006.

Kim, et al. Pretreatment and fractionation of corn stover by ammonia recycle percolation process. Bioresour Technol. Dec. 2005;96(18):2007-13.

Lloyd, et al, Combined sugar yields for dilute sulfuric acid pretreatment of corn stover followed by enzymatic hydrolysis of the remaining solids. Bioresour Technol. Dec. 2005;96(18):1967-77.

Mosier, et al. Features of promising technologies for pretreatment of lignocellulosic biomass. Bioresour Technol. Apr. 2005;96(6):673-86.

Mosier, et al. Optimization of pH controlled liquid hot water pretreatment of corn stover. Bioresour Technol. Dec. 2005;96(18):1986-93.

N. Dowe and J McMillan. 2001: SSF Experimental Protocols—Lignocallulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Nevoigt, et al. Osmoregulation and glycerol metabolism the yeast *Saccharomyces cerevisiae*. FEMS Microbiol Rev, Nov. 1997;21(3):23141.

Parekh, et al. Production of glycerol by hanseaula anomala. Biotechnol Bioeng. Jul. 1985;27(7):1089-91.

Shapouri et al. 2006. The Economic Feasibility of Ethanol Production From Sugar in the United States, USDA, 78 Pages, Jul. 2006.

Taylor. From Raw Sugar to Raw materials. Chemical innovation. 2000; 30:45-48.

USDA, "The Economic Feasibility of Ethanol Production From Sugar in the United States"; Jul. 2006, 69 pages.

Varbegyi et al., (1989, Kinetics of the thermal decomposition of cellulose, hemicellulose, and sugarcane bagasse. Energy Fuels, vol. 3, No. 3, pp. 329-335).

Waiss, et al. Improving Digestibility of Straws for Ruminant Feed by Aqueous Ammonia. Journal of Animal Science. 1972; 35(1):109-112.

Waltermann, at al. *Rhodococcus opacus* strain PD630 as a new source of high-value single-cell oil? Isolation and characterization of triacylglycerols and other storage lipids. Microbiology. 2000; 146;1143-1149.

METHOD TO PRODUCE SUGAR WATER AND ETHANOL

CROSS-REFERENCES TO RELATED APPLICATIONS/PATENTS

This application is a CON of Ser. No. 11/974,129 filed Oct. 11, 2007, now U.S. Pat. No. 8,323,923 B1, which claims benefit of 60/851,424 filed Oct. 13, 2006.

FIELD OF THE INVENTION

The invention relates generally to a method and system for producing ethanol and more particularly to a method and system for producing ethanol using one or more feedstock processing plants located near a feedstock producing or a feedstock storage site and an ethanol producing plant.

BACKGROUND OF THE INVENTION

It is known to use a variety of different types of feedstock to produce ethanol. It is also known to utilize a number of different methods for processing feedstock into ethanol. However, each of the different conventional methods suffer from one or more disadvantages, regardless, of the type of feedstock used to produce ethanol. For example, conventional methods for producing ethanol require raw, unprocessed feedstock to be transported from the site where the feedstock is produced or stored to a remote processing plant. Transportation of raw, unprocessed feedstock from the site of the feedstock producer to the ethanol producing plant results in substantial equipment, labor, fuel, maintenance and repair costs. More particularly, the transportation of raw, unprocessed feedstock results in an ethanol yield (by weight) of approximately 33% of the feedstock (by weight). In addition, the transportation of raw, unprocessed feedstock results in byproduct at the ethanol producing plant which amounts to approximately 33% (by weight) of the feedstock (by weight). Additional transportation costs, including labor, fuel, maintenance and repair, are incurred in connection with the removal of the byproducts from the ethanol producing plant. Further, conventional methods for producing ethanol require large storage capacities at either or both the site of the feedstock producer and the ethanol producing plant.

It would be desirable, therefore, if a method and system for producing ethanol could be provided that reduces the transportation costs associated with the production of ethanol from feedstock. It would also be desirable such a method and system could be provided that would reduce the tonnage of feedstock transported from a feedstock provider to an ethanol producer. It would be further desirable if such a method and system could be provided that would produce byproducts that may be left at the site of the feedstock provider to be used as animal feed, animal bedding, compost, biofuel, chemicals or the like. It would be a still further desirable if such a method and system could be provided that would produce a non-hazardous material to be transported from the feedstock provider to the ethanol producer. It would also be desirable if such a method and system could be provided that would reduce the storage requirements at an ethanol producing plant. It would be further desirable if such a method and system could be provided that would reduce or eliminate the environmental impact caused by the storage of feedstock, the disposal of byproducts, waste products and waste water, and the transportation of feedstock to an ethanol producing plant. It would be still further desirable if such a method and system could be produced that would reduce the size and cost of an ethanol producing plant and improve the efficiency of such a plant.

ADVANTAGES OF THE PREFERRED EMBODIMENTS OF THE INVENTION

It is an advantage of the preferred embodiments of the invention to provide a method and system for producing ethanol that reduces the transportation costs associated with the production of ethanol from feedstock. It is also an advantage of the preferred embodiments to provide a method and system that reduces the tonnage of feedstock transported from a feedstock provider to an ethanol producer. It is another advantage of the preferred embodiments to provide a method and system that produces byproducts that may be left at the site of the feedstock provider to be used as animal feed, animal bedding, compost, biofuel, chemicals or the like. It is still another advantage of the preferred embodiment to provide a method and system that produces a non-hazardous material to be transported from the feedstock provider to the ethanol producer. It yet another advantage of the preferred embodiments to provide a method and system that reduces the storage requirements at the ethanol producing plant. It is a further advantage of the preferred embodiments to provide a method and system that reduces or eliminates the environmental impact caused by the storage of feedstock, the disposal of byproducts, waste products and waste water, and the transportation of feedstock to an ethanol producing plant. It is a still further advantage of the preferred embodiments to provide a method and system that reduces the size and cost of an ethanol producing plant and improve the efficiency of such a plant.

Other advantages and features of this invention will become apparent from an examination of the drawings and the ensuing description.

EXPLANATION OF TECHNICAL TERMS

As used herein, the term "feedstock" shall refer to hard grains, starches, cellulose, hemicellulose and lignocellulosic biomasses such as corn stover, cereal straws, sugarcane bagasse, sawdust and paper pulp, waste materials, biomasses farmed for the sole purpose of producing ethanol such as switchgrass, old and/or poor quality animal feed, animal manure, paper, cardboard and the like. It is contemplated, however, that the term "feedstock" includes any material or substance that may be used to produce ethanol.

As used herein, the term "sugar water" shall refer to the substance produced by the one or more feedstock processing plants of the preferred embodiments of the present invention. More particularly, the term "sugar water" refers to the mixture of sugar and water produced by the mechanical destruction or grinding, the pretreatment, the liquefaction and the enzymolation of the feedstock followed by the separation of the wet animal feed. The term "sugar water" also refers to the concentrated form of the substance produced by the previously described process. It is also contemplated within the scope of the invention that the term "sugar water" may refer to a precursor substance of the concentrated form produced by the process described above. For example, the term "sugar water" may refer to the substance produced by the mechanical destruction or grinding of feedstock, or the term "sugar water" may refer to the substance produced by the mechanical destruction or grinding and the pretreatment of feedstock, or the term "sugar water" may refer to the substance produced by the mechanical destruction or grinding, the pretreatment and the liquefaction and the enzymolation of the feedstock. In the preferred embodiments of the present invention, the term "sugar water" refers to a non-hazardous, liquid-processed water precursor to ethanol.

SUMMARY OF THE INVENTION

The preferred embodiment of the invention comprises a method for producing ethanol. comprising the steps of providing feedstock, processing the feedstock at a feedstock processing plant adapted to produce sugar water and wet animal feed, separating the sugar water and wet animal feed, transporting the sugar water from the feedstock processing plant to an ethanol producing plant, and producing ethanol from the sugar water. In the preferred embodiments of the method for producing ethanol, the method further comprises the steps of pretreating the feedstock, concentrating, fermenting, distilling, dehydrating and denaturing the sugar water, and selling the ethanol. Also in the preferred embodiments of the invention, the feedstock is processed at or near a feedstock providing site.

The preferred embodiment of the invention further comprises a system for producing ethanol. The preferred system for producing ethanol comprises a feedstock provider adapted to provide feedstock, feedstock, a feedstock processing plant adapted to produce sugar water and wet animal feed from the feedstock, a means for transporting the sugar water, and an ethanol producing plant adapted to produce ethanol from the sugar water. In the preferred embodiments of the system for producing ethanol, the feedstock processing plant is located at or near the feedstock provider and produces a non-hazardous, non-fermented, and non-distilled materials. Also in the preferred embodiments of the system for producing ethanol, the ethanol producing plant is centrally located relative to a plurality of portable feedstock processing plants.

BRIEF DESCRIPTION OF THE DRAWINGS

The presently preferred embodiments of the invention are illustrated in the accompanying drawings, in which.

DESCRIPTION OF THE PREFERRED EMBODIMENTS OF THE INVENTION

Figure 1:
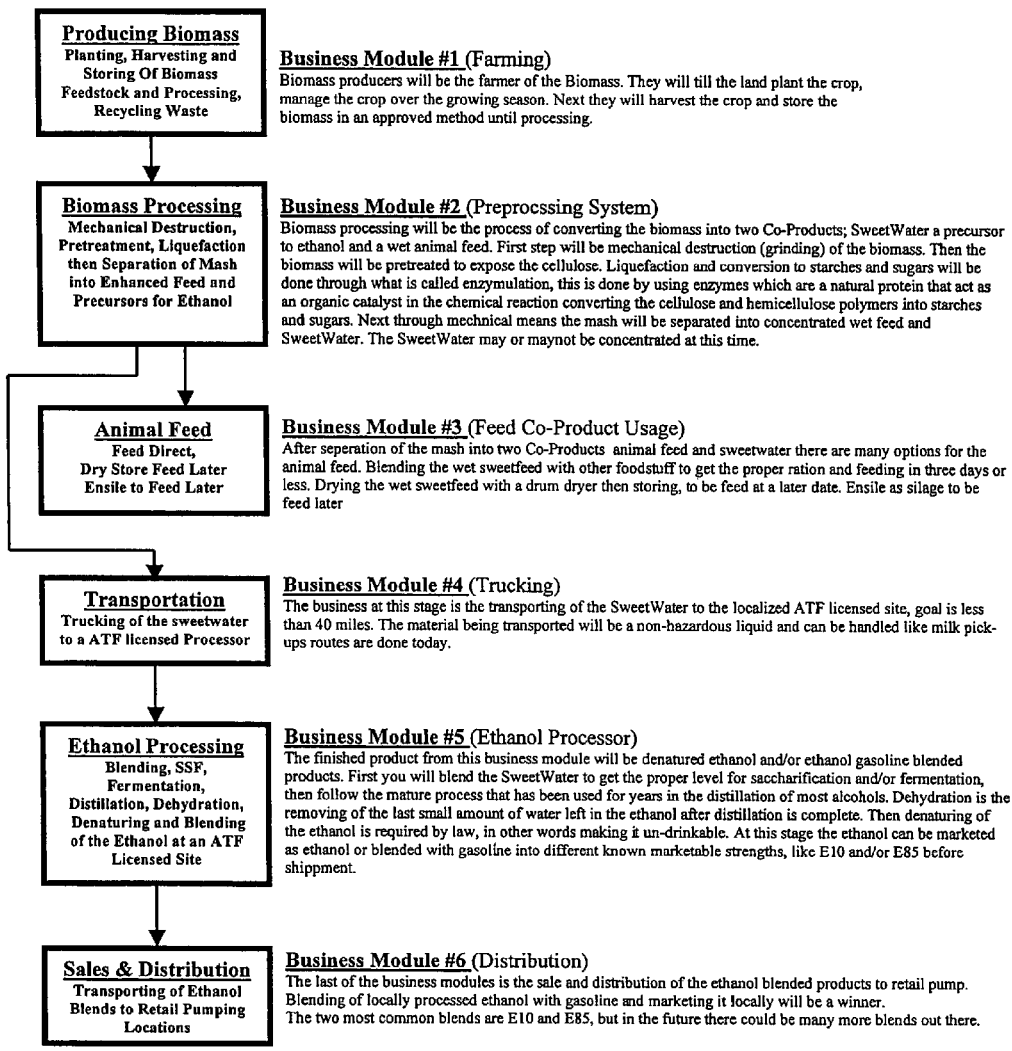
FIG. 1 is a schematic illustration outlining the steps and elements of the preferred method and system of the present invention.
Figure 2:
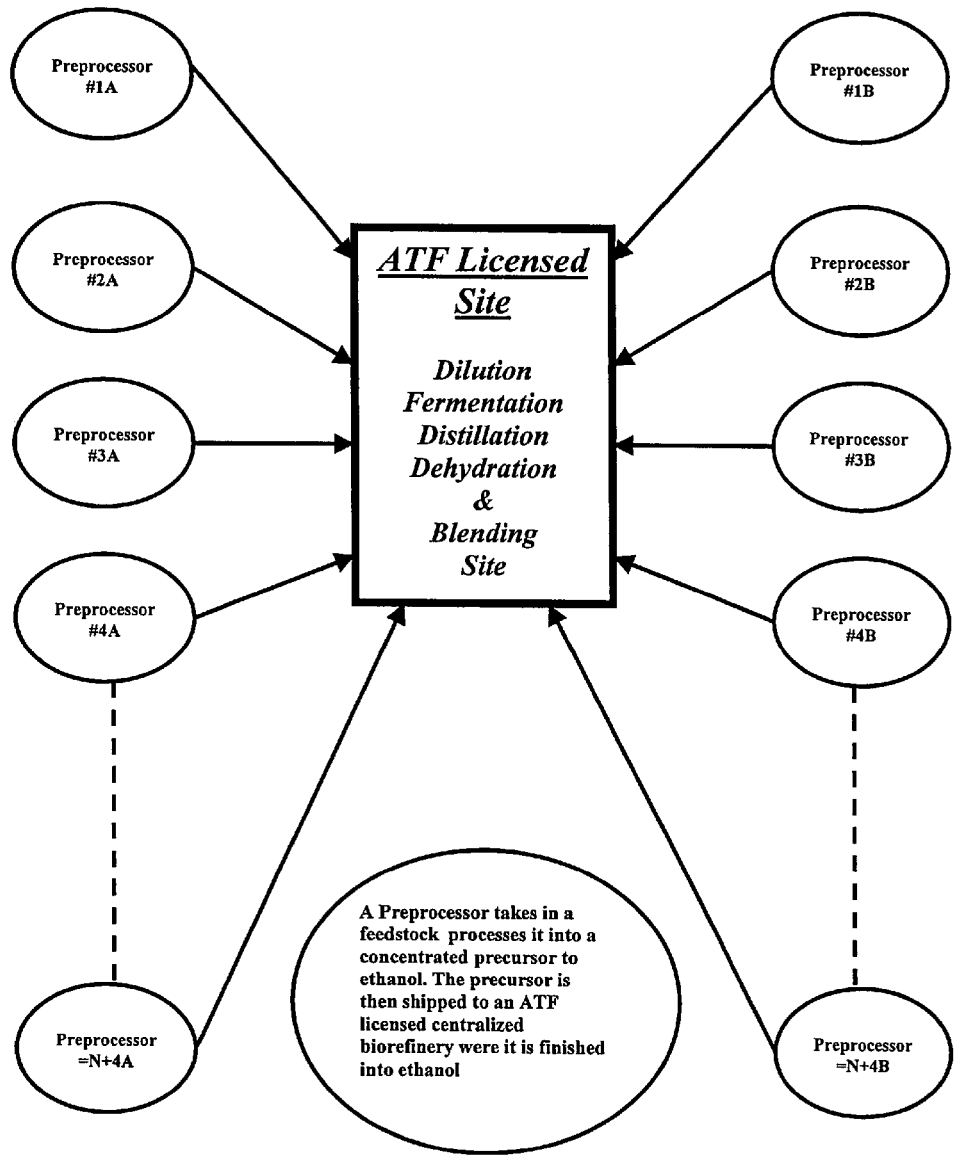
FIG. 2 is a schematic illustration of the plurality of feedstock processing plants and the ethanol producing plant of the preferred method and system of the present invention.

Referring now to the drawings, a preferred embodiment of the method and system in accordance with the present invention is illustrated in FIGS. 1 through 2. As shown in FIG. 1, the first step of the preferred method for producing ethanol is providing feedstock. Feedstock providers include farmers who plant, manage and harvest crops such as corn. Feedstock providers may also include feedstock storage facilities, food processors, recycle centers and other feedstock providing sites. Feedstock providers may also include those who specifically produce feedstock for the sole purpose of producing ethanol. The feedstock provided may include hard grains, cellulose biomasses, waste materials, biomasses farmed for the sole purpose of producing ethanol, old and/or poor quality animal feed, animal manure and the like. It is contemplated, however, that the feedstock provided may include any material or substance that may be used to produce ethanol. While FIG. 1 describes the preferred method and system for providing feedstock, it is contemplated within the scope of the invention, however, that any suitable method and system for providing feedstock may be used.

Still referring to FIG. 1, the second step of the preferred method and system for producing ethanol is processing the feedstock. The preferred processing of feedstock step is performed at a feedstock providing site. As a result, it is contemplated that the preferred method and system for producing ethanol will include a plurality of feedstock processing plants located at or near feedstock providing sites. The preferred feedstock processing plants are non-fermenting, non-distilling plants that do not require a license to operate from the United States Department of Alcohol Tobacco and Firearms ("ATF"). Further, the preferred feedstock processing plants produce non-hazardous materials that may be transported as such. Still further, the preferred feedstock processing plants may be portable. The portability of the preferred feedstock processing plant contributes to the transportation cost savings provided by the present invention.

Still referring to FIG. 1, the preferred processing step converts the feedstock into two products; namely, sugar water and wet animal feed. The feedstock may be processed in any number of ways including the following: (1) mechanical destruction (grinding) of the feedstock; (2) pretreatment of the feedstock; and (3) enzymolation, enzymolosis or enzymatic hydrolysis of the feedstock. The pretreatment of the feedstock may include dilute-acid thermochemical pretreatment adapted to hydrolyze the feedstock and break down the feedstock into its component sugars, e.g., xylose, etc. The pretreatment of the feedstock may also solubize a portion of the lignin. Processing of the feedstock also includes enzymatic hydrolysis in which enzymes are used to convert cellulosic biomass into fermentable sugars. More particularly, enzymatic hydroloysis is adapted to release the feedstock's sugars, e.g., glucose. The preferred pretreatment is adapted to make the cellulose of the feedstock more accessible to further treatment. In the preferred embodiment of the method and system for producing ethanol, the sugars of the pretreated feedstock are later fermented into fuel ethanol and the residue lignin may be used for catalytic conversion to other products, gasified or combusted to provide heat and power for the plant operation or for sale.

Still referring to FIG. 1, the processing of feedstock step of the preferred method may also include concentrating the precursor/sugar water. The processing of feedstock step of the preferred method and system for producing ethanol described in FIG. 1 reduces the transportation costs associated with the production of ethanol from feedstock as described in more detail below. While FIG. 1 describes the preferred method and system for processing feedstock, it is contemplated within the scope of the invention that any suitable method for processing feedstock may be used.

Referring still to FIG. 1, the third step of the preferred method and system for producing ethanol is separating the precursor/sugar water and wet animal feed. As described in FIG. 1, the wet animal feed has multiple uses. In addition, the separation of the wet animal feed from the precursor/sugar water further reduces the transporation costs associated with the production of ethanol from feedstock as described in more detail below.

Still referring to FIG. 1, the fourth step of the preferred method and system for producing ethanol is transporting the sugar water from the feedstock processing plant or plants to the ethanol producing plant. In the most preferred embodiment of the method and system for producing ethanol, the tonnage that is shipped from the feedstock processing plant to the ethanol producing plant is 100% usable material. Any byproducts generated at the feedstock processing plant may be used as animal feed, animal bedding or compost, biofuel, chemicals or they be land applied. Further, in the preferred embodiments of the method and system for producing ethanol, the precursor/sugar water produced by the feedstock processing plant or plants is a non-hazardous material with relatively few transportation restrictions.

As noted above, steps two and three of the preferred method and system for producing ethanol substantially reduce the transportation costs. More particularly, instead of transporting raw, non-processed feedstock from the feedstock providing site, the preferred method and system for producing ethanol requires that only processed feedstock or precursor/sugar water be transported from the feedstock providing site to the ethanol producing plant. As a result, tonnage and costs such as labor, fuel, repair and maintenance are reduced. By way of example, it is estimated that approximately tonnage may be reduced by approximately 66% to 75% using the preferred method and system for producing ethanol. In addition, storage capacity at the ethanol producing plant may be reduced, thereby minimizing or eliminating the adverse environmental impact caused by storage of feedstock. It is estimated that the total transportation costs associated with incoming feedstock and outgoing byproducts or waste materials may be reduced by approximately 80% using the preferred method and system for producing ethanol.

Still referring to FIG. 1, the fifth step of the preferred method and system for producing ethanol is producing ethanol. The finished product may be denatured ethanol or an ethanol and gasoline blend. In the preferred embodiment of the method and system for producing ethanol, ethanol is produced at an ethanol producing plant from sugar water transported from one or more feedstock processing plants. The preferred ethanol producing plant is a centrally-located (relative to a plurality of feedstock processing plants) site which receives concentrated sugar water from feedstock processing plants and blends the sugar water to the proper sugar level for fermentation. Because ethanol is a form of alcohol, any producer must be licensed by the United States Department of Alcohol Tobacco and Firearms ("ATF"). The fermentation process produces what is commonly referred to as beer. More particularly, the fermentation process yields ethanol and carbon dioxide. After the completion of the fermentation step, the beer is then preferably distilled and dehydrated into 200 proof ethanol by removing the remaining amount of water in the liquid. In the preferred embodiment, the final step is called denaturing which is a process for making the liquid unfit for human consumption. The wastewater produced by the process may be used to dilute the concentrated sugar water, thereby avoiding and/or reducing treatment requirements. Because the feedstock tonnage transported to the ethanol producing plant is reduced during the feedstock processing and separating steps of the preferred method for producing ethanol, the size, land acquisition cost and plant construction cost of the ethanol producing plant may be reduced.

While FIG. 1 illustrates the preferred processes performed at the ethanol producing plant, it is contemplated within the scope of the invention that one or more of these processes may be performed at the one or more feedstock processing plants. In such case, it may be necessary to obtain an ATF license for each such feedstock processing plant. In the alternative, one or more of the processes performed in the first three steps of the preferred method and system for producing ethanol may be performed at the ethanol producing plant. Further, while FIG. 1 illustrates the preferred processes for converting sugar water into ethanol, it is contemplated within the scope of the invention that any suitable process for converting sugar water into ethanol may be used.

Still referring to FIG. 1, the sixth step of the preferred method and system for producing ethanol is selling and distributing the ethanol or ethanol blended products produced at the ethanol producing plant. In the preferred embodiment of the method and system for producing ethanol, the ethanol and ethanol blended products are sold and distributed to retail liquid fuel pumping locations. It is contemplated within the scope of the invention that ethanol and ethanol blended products may be sold and distributed to any suitable purchaser and/or distributor. At the present time, the two most common ethanol blended products are E10 and E85. However, it is contemplated that the preferred embodiments of the method and system for producing ethanol may be used to produce many other different blends in the future. In addition, it is contemplated within the scope of the invention that the preferred embodiments of the method and system for producing ethanol may be used to produce wet cattle feed, dry cattle feed, 190 proof ethanol, 200 proof ethanol, direct injection fuel and liquid carbon dioxide.

As shown in FIG. 2, the preferred method and system for producing ethanol employs a plurality of feedstock processing plants and a centrally-located, ATF-licensed ethanol producing plant. According to the preferred embodiments of the method and system for producing ethanol, feedstock is processed into sugar water at the plurality of feedstock processing plants. Thereafter, the precursor/sugar water is transported to the centrally-located, ATF-licensed ethanol producing plant where it is converted into ethanol. While FIG. 2 illustrates a plurality of feedstock processing plants, it is also contemplated within the scope of the invention that only one feedstock processing plant may be employed in accordance with the present invention. In addition, while FIG. 2 identifies certain processes performed at the plurality of feedstock processing plants and other processes performed at the centrally-located ethanol producing plant, it is also contemplated within the scope of the invention that fewer or more processes may be performed at the plurality of feedstock processing plants and fewer or more processes may be performed at the centrally-located ethanol producing plant.

In use, several advantages of the preferred embodiments of the method and system for producing ethanol are achieved. For example, the preferred embodiments of the invention provide a method and system for producing ethanol that reduces the transportation costs associated with the production of ethanol from feedstock. The preferred embodiments also provide a method and system that reduces the tonnage of feedstock transported from a feedstock provider to an ethanol producer. The preferred embodiments further provide a method and system that produces byproducts that may be left at the site of the feedstock provider to be used as animal feed, animal bedding, compost, biofuel, chemicals or the like. In addition, the preferred embodiments provide a method and system that produces a non-hazardous material to be transported from the feedstock provider to the ethanol producer. The preferred embodiments also provide a method and system that reduces the storage requirements at the feedstock processor plants and the ethanol producer plant. The preferred embodiments further provide a method and system that reduces or eliminates the environmental impact caused by the storage of feedstock, the disposal of byproducts, waste products and waste water, and the transportation of feedstock to an ethanol producing plant. The preferred embodiments still further provide a method and system that reduces the size and cost of an ethanol producing plant and improve the efficiency of such a plant.

In addition, the preferred embodiments provide a method and system that utilizes largely untapped resources as feedstock. The feedstock utilized by the preferred embodiments is more abundant, less costly to produce and contains greater potential energy than feedstock that is more commonly utilized in the production of ethanol. The preferred embodiments provide a method and system that allows feedstock providers to utilize the byproducts of the feedstock processing and derive revenue from feedstock sources that have traditionally been treated as waste.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A distributed production method for producing sugar water and ethanol, the method comprising the steps of:
   a) providing a feedstock comprising cellulose, hemicellulose, and/or lignocellulose to each of a plurality of portable feedstock processing plants each of which is located at or near a feedstock providing site;
   b) processing the cellulose, hemicellulose, and/or lignocellulose of the feedstock at the plurality of portable feedstock processing plants to produce a sugar water and one or more byproducts, wherein the processing comprises mechanical destruction, pretreatment, and/or enzymatic hydrolysis;
   c) separating the sugar water produced from the cellulose, hemicellulose, and/or lignocellulose from the one or more byproducts at the plurality of portable feedstock processing plants;
   d) concentrating the separated sugar water at the plurality of portable feedstock processing plants;
   e) transporting the concentrated sugar water from the plurality of portable feedstock processing plants to a centralized ethanol producing plant; and
   f) producing ethanol from the transported sugar water at the centralized ethanol producing plant.

2. A distributed production method for producing sugar water and ethanol, the method comprising the steps of:
   a) providing a feedstock comprising cellulose, hemicellulose, and/or lignocellulose to each of a plurality of portable feedstock processing plants each of which is located at or near a feedstock providing site;
   b) processing the cellulose, hemicellulose, and/or lignocellulose of the feedstock at the plurality of portable feedstock processing plants to produce a sugar water and one or more byproducts, wherein the processing comprises mechanical destruction, pretreatment, and/or enzymatic hydrolysis;
   c) separating the sugar water produced from the cellulose, hemicellulose, and/or lignocellulose from the one or more byproducts at the plurality of portable feedstock processing plants;
   d) transporting the separated sugar water from the plurality of portable feedstock processing plants to a centralized ethanol producing plant; and
   e) producing ethanol from the transported sugar water at the centralized ethanol producing plant.

3. A distributed production method for producing sugar water and ethanol, the method comprising the steps of:
   a) providing a feedstock comprising cellulose, hemicellulose, and/or lignocellulose to each of a plurality of portable feedstock processing plants each of which is located at or near a feedstock providing site;
   b) processing the cellulose, hemicellulose, and/or lignocellulose of the feedstock at the plurality of portable feedstock processing plants to produce a sugar water comprising xylose, and one or more byproducts and/or byproducts, wherein the processing comprises mechanical destruction, dilute-acid thermochemical treatment, and enzymatic hydrolysis;
   c) separating the sugar water comprising xylose from the one or more products and/or byproducts at the plurality of portable feedstock processing plants;
   d) concentrating the separated sugar water at the plurality of portable feedstock processing plants;
   e) transporting the concentrated sugar water from the plurality of portable feedstock processing plants to a centralized ethanol producing plant; and
   f) producing ethanol from the transported sugar water at the centralized ethanol producing plant.

4. A distributed production method for producing sugar water and ethanol, the method comprising the steps of:
   a) providing a feedstock comprising cellulose, hemicellulose, and/or lignocellulose to each of a plurality of portable feedstock processing plants each of which is located at or near a feedstock providing site;
   b) processing the cellulose, hemicellulose, and/or lignocellulose of the feedstock at the plurality of portable feedstock processing plants to produce glucose in a sugar water, and one or more byproducts and/or byproducts, wherein the processing comprises mechanical destruction, dilute-acid thermochemical treatment, and enzymatic hydrolysis;
   c) separating the sugar water from the one or more products and/or byproducts at the plurality of portable feedstock processing plants;
   d) concentrating the separated sugar water at the plurality of portable feedstock processing plants;
   e) transporting the concentrated sugar water from the plurality of portable feedstock processing plants to a centralized ethanol producing plant; and
   f) producing ethanol from the transported sugar water at the centralized ethanol producing plant.

5. The method of claim 1, wherein the feedstock comprising cellulose, hemicellulose, and/or lignocellulose is corn stover, cereal straws, sugarcane bagasse, sawdust, paper pulp, waste materials, switchgrass, animal feed, animal manure, paper, cardboard, or a combination thereof.

6. The method of claim 1, wherein the one or more byproducts are used as animal feed, animal bedding, or compost.

7. The method of claim 1, wherein the pretreatment comprises dilute-acid thermochemicat treatment.

8. The method of claim 1, further comprising providing the plurality of portable feedstock processing plants.

9. The method of claim 1, wherein the feedstock providing site provides the feedstock comprising cellulose, hemicellulose, and/or lignocellulose to a portable feedstock processing plant.

10. The method of claim 1, wherein the processing comprises hydrolysis of the cellulose, hemicellulose, and/or lignocellulose to one or more component sugars.

11. The method of claim 10, wherein the one or more component sugars comprise xylose.

12. The method of claim 10, wherein the one or more component sugars comprise glucose.

13. The method of claim 2, wherein the feedstock comprising cellulose, hemicellulose, and/or lignocellulose is corn stover, cereal straws, sugarcane bagasse, sawdust, paper pulp, waste materials, switchgrass, animal feed, animal manure, paper, cardboard, or a combination thereof.

14. The method of claim 2, wherein the one or more byproducts are used as animal feed, animal bedding, or compost.

15. The method of claim 2, wherein the pretreatment comprises dilute-acid thermochemicat treatment.

16. The method of claim 2, further comprising providing the plurality of portable feedstock processing plants.

17. The method of claim 2, wherein the feedstock providing site provides the feedstock comprising cellulose, hemicellulose, and/or lignocellulose to a portable feedstock processing plant.

18. The method of claim 2, wherein the processing comprises hydrolysis of the cellulose, hemicellulose, and/or lignocellulose to one or more component sugars.

19. The method of claim 18, wherein the one or more component sugars comprise xylose.

20. The method of claim 18, wherein the one or more component sugars comprise glucose.

* * * * *